(12) United States Patent
Caballero

(10) Patent No.: US 10,905,791 B1
(45) Date of Patent: Feb. 2, 2021

(54) MOBILE AIR SANITIZER

(71) Applicant: Cesar Caballero, Oak Hills, CA (US)

(72) Inventor: Cesar Caballero, Oak Hills, CA (US)

( * ) Notice: Subject to any disclaimer, the term of this patent is extended or adjusted under 35 U.S.C. 154(b) by 0 days.

(21) Appl. No.: 17/014,822

(22) Filed: Sep. 8, 2020

Related U.S. Application Data

(60) Provisional application No. 63/031,151, filed on May 28, 2020.

(51) Int. Cl.
*A61L 9/20* (2006.01)
*A61L 9/014* (2006.01)

(52) U.S. Cl.
CPC .............. *A61L 9/20* (2013.01); *A61L 9/014* (2013.01); *A61L 2209/12* (2013.01)

(58) Field of Classification Search
None
See application file for complete search history.

(56) References Cited

U.S. PATENT DOCUMENTS

2017/0321877 A1* 11/2017 Polidoro ............... F21S 8/033

* cited by examiner

*Primary Examiner* — Jelitza M Perez
(74) *Attorney, Agent, or Firm* — Plager Schack LLP; Mark H. Plager; Kara Verryt

(57) ABSTRACT

An air sanitizer for sanitizing air and neutralizing pathogens in the air may include an air inlet attached to a first chamber including at least one first chamber UV-C light positioned therein; a second chamber operatively attached to the first chamber, the second chamber including a nano-technology decoy positioned therein; a third chamber operatively attached to the second chamber, the third chamber including at least one third chamber UV-C light positioned therein; and an air outlet operatively connected to the third chamber. The nano-technology decoy may be a dendritic polymer mesh covered with sialic acid.

10 Claims, 5 Drawing Sheets

MOBILE AIR SANITIZER

RELATED APPLICATION

This application claims priority to provisional patent application U.S. Ser. No. 63/031,151 filed on May 28, 2020, the entire contents of which is herein incorporated by reference.

BACKGROUND

The embodiments described herein relate generally to decontamination and sanitization devices and, more particularly, to a mobile air sanitizer for sanitizing air from dangerous pathogens, such as viruses.

Existing air cleaning devices filter the air, but do not neutralize pathogens. Some existing devices use ionizers that create ozone, which is not healthy for humans.

Therefore, what is needed is a mobile air sanitizer that can filter air and neutralize pathogens safely without creating ozone.

SUMMARY

Some embodiments of the present disclosure include an air sanitizer for sanitizing air and neutralizing pathogens in the air. The air sanitizer may include an air inlet attached to a first chamber including at least one first chamber UV-C light positioned therein; a second chamber operatively attached to the first chamber, the second chamber including a nano-technology decoy positioned therein; a third chamber operatively attached to the second chamber, the third chamber including at least one third chamber UV-C light positioned therein; and an air outlet operatively connected to the third chamber. The nano-technology decoy may be a dendritic polymer mesh covered with sialic acid.

BRIEF DESCRIPTION OF THE FIGURES

The detailed description of some embodiments of the invention is made below with reference to the accompanying figures, wherein like numerals represent corresponding parts of the figures.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used as an air sanitizer and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

The various elements of the present disclosure may be related in the following exemplary fashion. It is not intended to limit the scope or nature of the relationships between the various elements and the following examples are presented as illustrative examples only.

Figure 1:
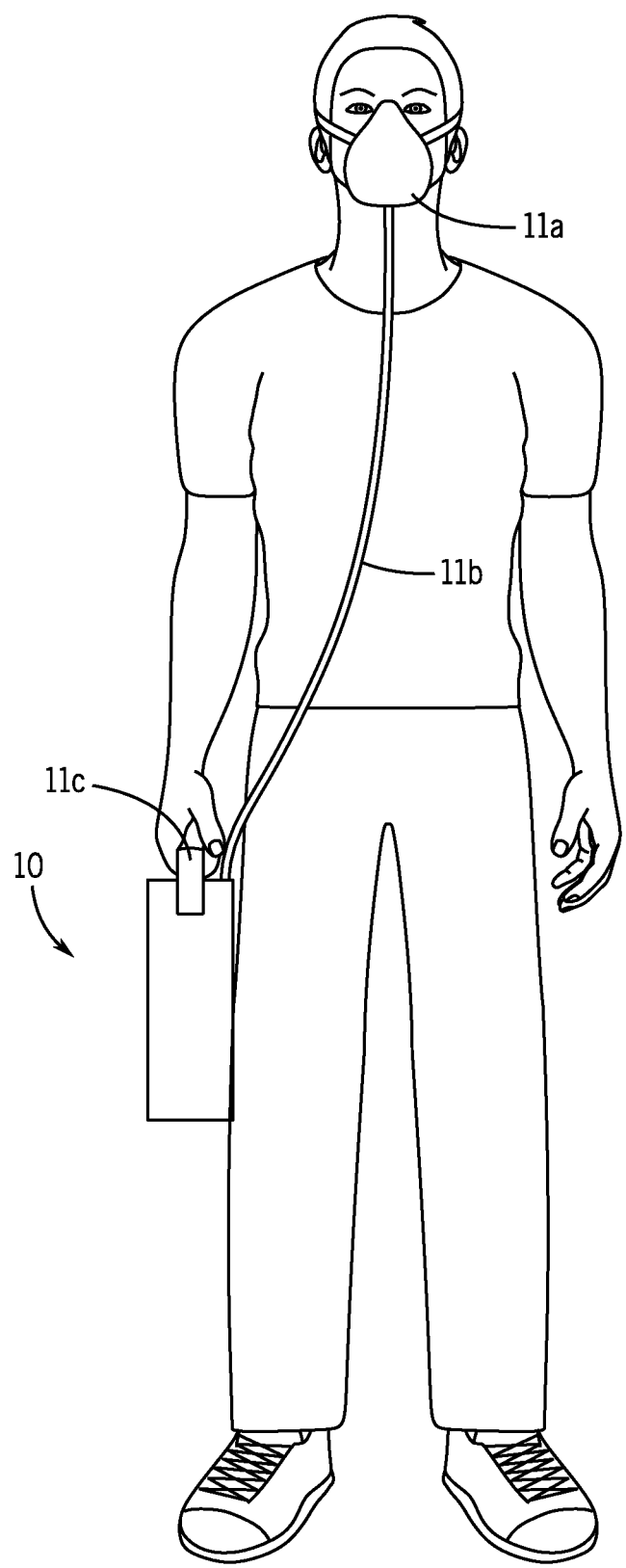
FIG. 1 is a front perspective view of one embodiment of the present disclosure.
Figure 2:
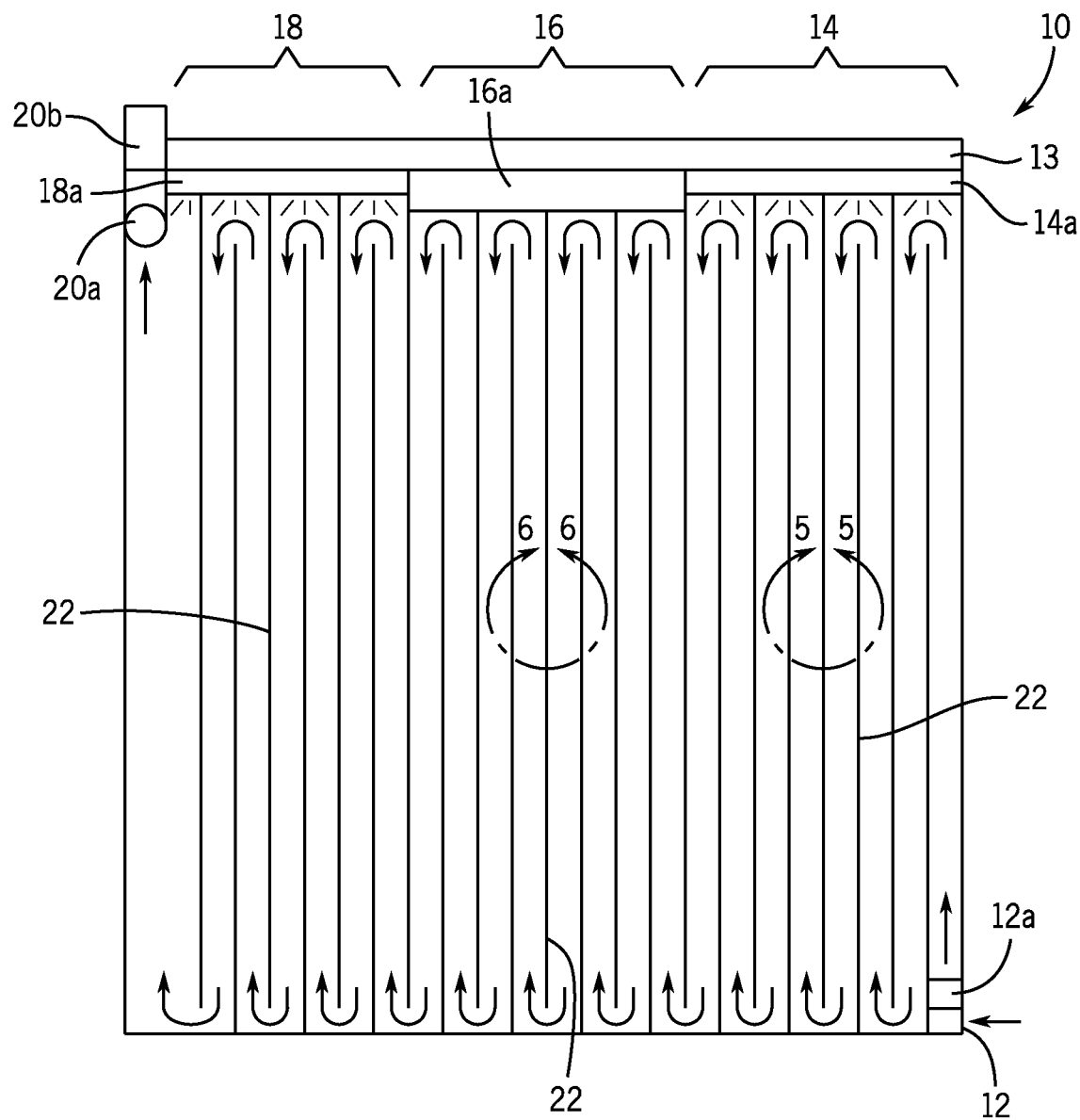
FIG. 2 is a schematic front elevation view of one embodiment of the present disclosure.
Figure 7:
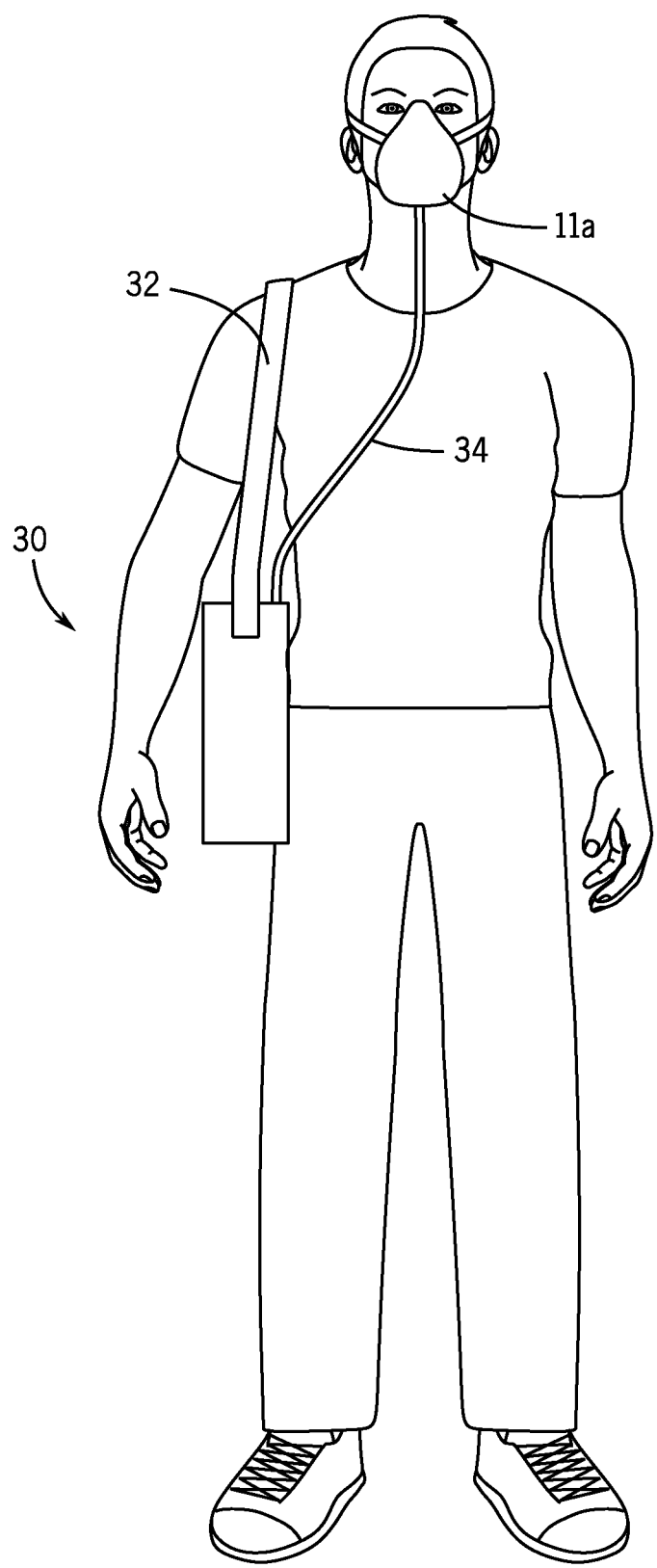
FIG. 7 is a front perspective view of one embodiment of the present disclosure.

By way of example, and referring to FIGS. 1-7, some embodiments of the invention include a mobile air sanitizer 10 for sanitizing air and neutralizing pathogens in the air, the mobile air sanitizer 10 comprising a housing comprising an air inlet 12 with an air filter 12a attached to a first chamber 14 comprising at least one first chamber UV-C light 14a; a second chamber 16 operatively attached to the first chamber 14, the second chamber 16 including a nano-technology decoy; a third chamber 18 operatively attached to the second chamber 16, the third chamber 18 comprising at least one third chamber UV-C light 18a; and a sanitized air outlet 20b operatively attached to the third chamber 18, wherein air flows into the mobile air sanitizer 10 through, in order, the air inlet 12, the first chamber 14, the second chamber 16, and the third chamber 18 and out of the mobile air sanitizer 10 through the air outlet 20b. In some embodiments, the mobile air sanitizer 10 may further comprise a check valve 20a or other air valve for preventing backflow of the air, the check valve 20a being positioned before the air outlet 20b. While not shown in the Figures, some embodiments of the mobile air sanitizer 10 may further comprise a pump to assist with airflow therethrough. Further, as shown in the Figures, the mobile air sanitizer 10 may comprise a housing designed to house the chambers, wherein the housing may include an openable lid 13. In some embodiments, the lid 13 may include an outlet orifice extending therethrough and positioned to align with the air outlet 20b, wherein an air supply tube 11b may be attached to the air outlet 20b and extend through the orifice in the lid. A distal end of the air supply tube 11b may be attached to, for example, a face mask 11a worn by a user to direct the sanitized air directly to the user's nose and mouth. As shown in FIG. 1, the mobile air sanitizer 10 may comprise a handle 11c attached to an exterior of the housing, wherein the user may use the handle 11c to carry the mobile air sanitizer 10. Alternatively, as shown in FIG. 7, the mobile air sanitizer 30 may comprise a shoulder strap 32 extending from an exterior of the housing to allow a user to easily carry the mobile air sanitizer 30. The use of other carrying means are also envisioned.

As described above, the mobile air sanitizer 10 may comprise an air inlet 12 attached to the first chamber 14. In some embodiments, the air inlet 12 may be attached to a filter 12a, and the air inlet 12 may allow for air to enter the mobile air sanitizer 10 and flow into the first chamber 14. As also described above, the first chamber 14 may include at least one UV-C light 14a positioned therein. In some embodiments, the UV-C light 14a may have a wavelength of about 260 nm. In embodiments, the UV-C light 14a may be operatively attached to a power source, such as a battery 16a.

Once it has passed through the first chamber 14, air may flow into the second chamber 16. The second chamber 16 may comprise a nano-technology decoy. For example, the nano-technology decoy may comprise a decoy mesh 26, such as a dendritic polymer mesh, covered with sialic acid (N-acetylneuraminic acid) 28. Pathogens in the air may be attracted to the sialic acid and, thus, may get trapped within the dendritic polymer mesh, where pathogens would release their DNA and become neutralized.

After leaving the second chamber 16, air may flow into the third chamber 18. The third chamber 18 may comprise at least one UV-C light 18a positioned therein, wherein the UV-C light 18a may have a wavelength of about 260 nm. Additionally, the UV-C light 18a may be operatively attached to the power source. From the third chamber 18, air may flow past a check valve 20a and through the air outlet 20b to leave the mobile air sanitizer 10. The air outlet 20b may include an air tube connector, which may be used to connect the mobile air sanitizer 10 to an air supply tube 11b to feed sanitized air to the desired location, such as to a breather face mask 11a, as described above.

Figure 5:
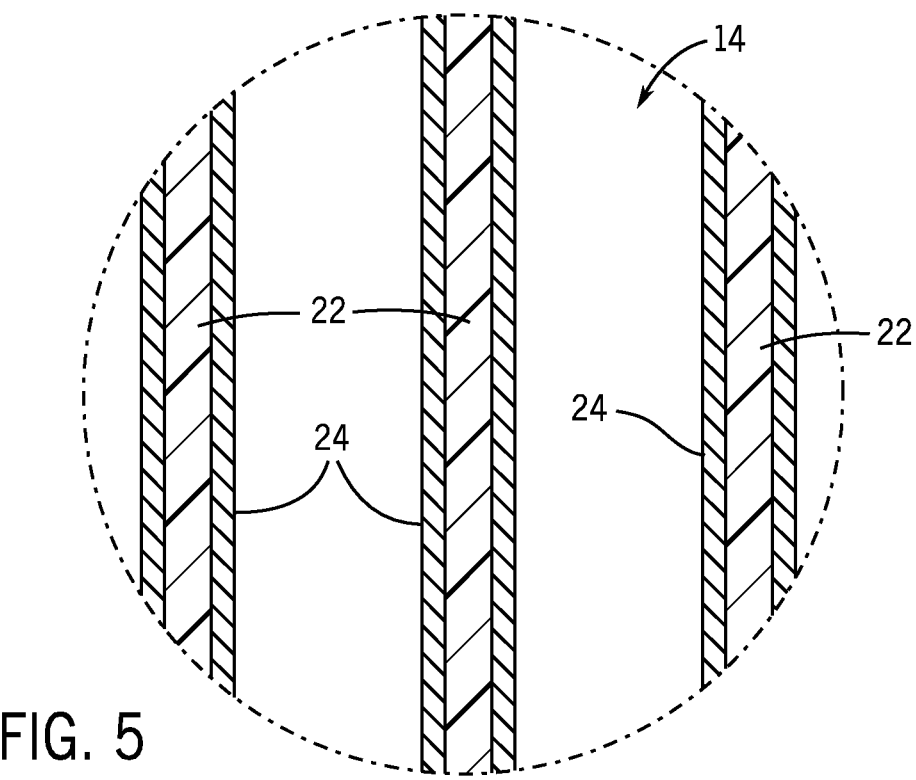
FIG. 5 is a detail cross-sectional view of one embodiment of the present disclosure, taken along line 5-5 in FIG. 2.
Figure 6:
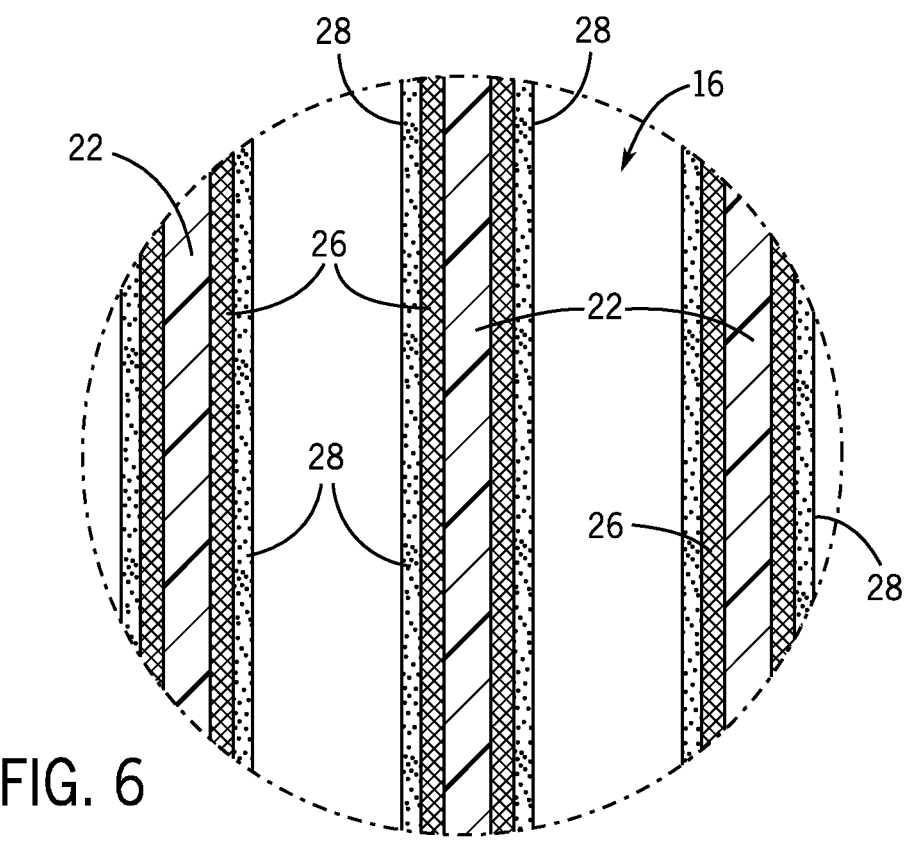
FIG. 6 is a detail cross-sectional view of one embodiment of the present disclosure, taken along line 6-6 in FIG. 2.

As shown in the Figures, each of the chambers 14, 16, 18 may comprise a plurality of baffles 22 positioned therein, creating a maze-like structure forcing the air to snake through each of the chambers 14, 16, 18. In some embodiments, the baffles 22 may result in the air taking at least about 8 passes through each of the chambers, wherein the air is in each chamber for at least about 30 seconds. The chambers and baffles 22 may be made of any suitable material. In some embodiments, the baffles 22 comprise a plastic material. In the first chamber 14 and the third chamber 18 (i.e., the chambers that include UV-C lights), the baffles 22 may be lined or covered with a reflective material, such as aluminum foil 24, as shown in FIG. 5. In the second chamber 16, the baffles 22 may be lined with a layer of the dendritic polymer mesh 26 followed by a lining of the sialic acid 28. However, in other embodiments, the dendritic polymer mesh 26 with the sialic acid covering 28 may fill the spaces between each of the baffles 22.

As mentioned above, the chambers 14, 16, 18 may be fitted into a housing, which may comprise, for example, a plastic box. In a particular embodiment, the housing may be about 12 inches wide, about 3¾ inches deep, and about 10 inches long, and the air sanitizer 10 may hold about 6.5 quarts of air by volume. However, the mobile air sanitizer may, of course, be scaled up or down as necessary. In embodiments, a top side of the first chamber 14 and the third chamber 18 may be open within the housing to allow for the placement of the UV-C lights 14a, 18a, while a power source may cover the top of the second chamber 16. As shown in the Figures, both the first chamber UV-C light 14a and the third chamber UV-C light 18a may be attached to a single power source. In some embodiments, once all of the electrical and other components are in place and checked to make sure they work, the housing may be hermetically sealed to prevent leakage (in or out) of potentially contaminated air.

Figure 3:
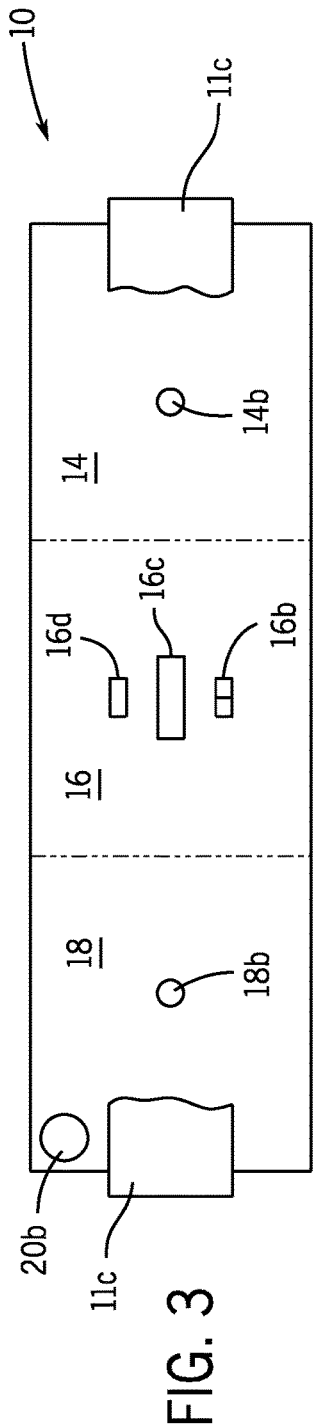
FIG. 3 is a top plan view of one embodiment of the present disclosure.
Figure 4:
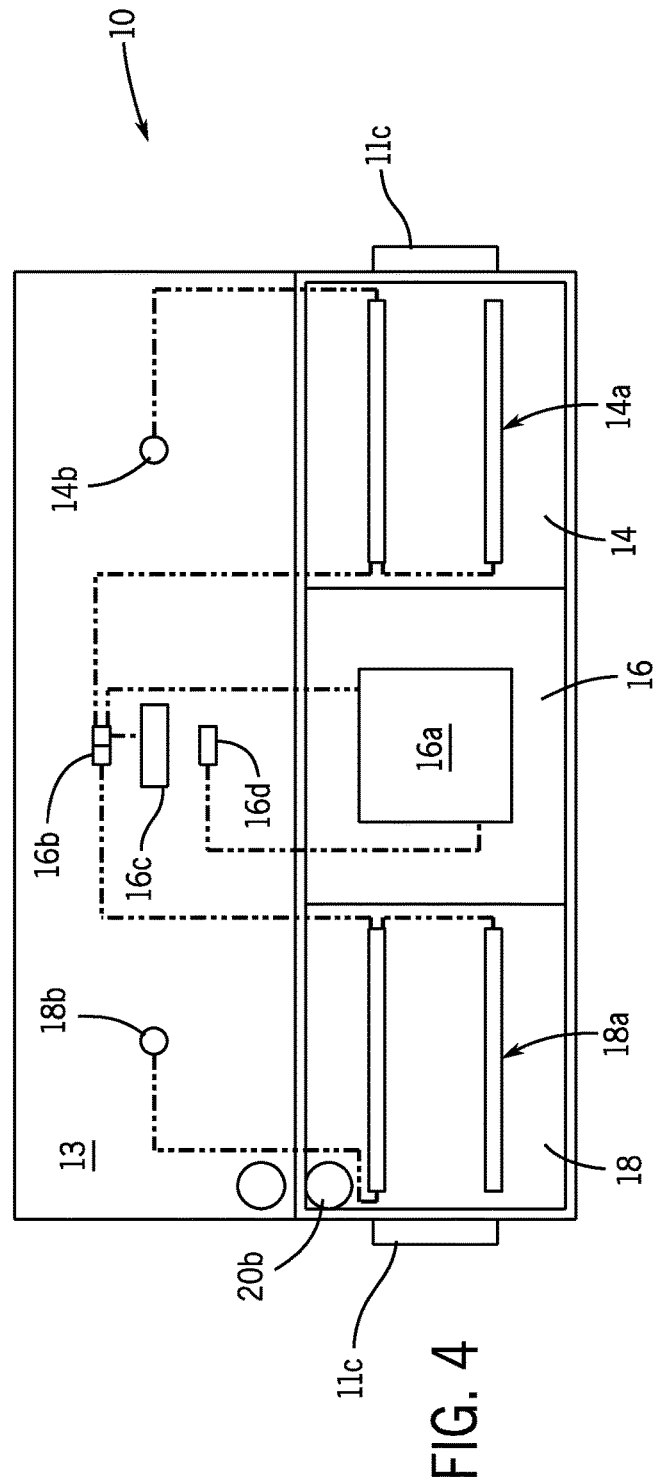
FIG. 4 is a top plan view of one embodiment of the present disclosure.

As shown in FIGS. 3 and 4, some embodiments of the mobile air sanitizer 10 include controls and indicators. For example, the first chamber UV-C light 14a may have a first chamber on indicator light 14b attached thereto, wherein the first chamber on indicator light 14b illuminates when the first chamber UV-C light 14a is illuminated. Similarly, the third chamber UV-C light 18a may have a third chamber on indicator light 18b attached thereto, wherein the third chamber on indicator light 18b illuminates when the third chamber UV-C light 18a is illuminated. A UV light switch 16b may also be operatively attached to each of the UV-C lights 14a, 18a, wherein the UV light switch 16b provides a mechanism for a user to turn the mobile air sanitizer 10 on and off. The battery 16a may also be operatively attached to a battery charge indicator 16c which may provide the user with a visual indication of the charging level of the battery 16a. Furthermore, the mobile air sanitizer 10 may further comprise a battery charging port 16d operatively attached to the battery 16a, wherein the charging port 16d may allow the battery 16a to be charged without requiring removal thereof.

While it is mentioned above that the mobile air sanitizer may be used to connect to a breather mask, the intended use is not particularly limited. Rather, the mobile air sanitizer may be scaled up to sanitize air in a car, plane, train, a house, hospital, school, or the like. The device may be worn and carried in a backpack or a shoulder bag. To use the device, the air outlet would simply be operatively connected to the desired location for the sanitized air. For example, a person, such as a first responder or health professional, may attach the device to a breather mask and simply breathe as normal to breathe sanitized air, free of viruses and other pathogens.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. An air sanitizer for sanitizing air and neutralizing pathogens in the air, the air sanitizer comprising:
   an air inlet attached to a first chamber comprising at least one first chamber UV-C light positioned therein;
   a second chamber operatively attached to the first chamber, the second chamber including a nano-technology decoy positioned therein;
   a third chamber operatively attached to the second chamber, the third chamber comprising at least one third chamber UV-C light positioned therein; and
   an air outlet operatively connected to the third chamber.

2. The air sanitizer of claim 1, further comprising a check valve positioned between the third chamber and the air outlet.

3. The air sanitizer of claim 1, wherein the nano-technology decoy comprises a decoy mesh covered with sialic acid.

4. The air sanitizer of claim 3, wherein the decoy mesh comprises a dendritic polymer mesh.

5. The air sanitizer of claim 1, wherein the first chamber, the second chamber, and the third chamber each comprise a plurality of baffles positioned therein, creating a maze-like structure within each of the chambers.

6. The air sanitizer of claim 5, wherein the baffles in each of the first chamber and the third chamber are lined with a reflective material.

7. The air sanitizer of claim 5, wherein:
   the baffles in the third chamber are lined with the nano-technology decoy; and
   the nano-technology decoy comprises a dendritic polymer mesh covered with sialic acid.

8. The air sanitizer of claim 5, wherein:
   a space between adjacent baffles within the second chamber is filled with the nano-technology decoy; and
   the nano-technology decoy comprises a dendritic polymer mesh covered with sialic acid.

9. The air sanitizer of claim 1, further comprising a power source operatively attached to the first chamber UV-C light and the third chamber UV-C light.

10. The air sanitizer of claim 9 further comprising:
- a first chamber on indicator light operatively attached to the power source and to the first chamber UV-C light;
- a third chamber on indicator light operatively attached to the power source and to the third chamber UV-C light; and
- a UV light switch operatively attached to the power source, the first chamber UV-C light, and the third chamber UV-C light.

* * * * *